US006197747B1

(12) United States Patent
Watrud et al.

(10) Patent No.: US 6,197,747 B1
(45) Date of Patent: Mar. 6, 2001

(54) **INSERTION OF THE *BACILLUS THURINGIENSIS* CRYSTAL PROTEIN GENE INTO PLANT COLONIZING MICROORGANISMS AND THEIR USE**

(75) Inventors: Lidia S. Watrud, Maryland Heights; Frederick J. Perlak, St. Louis, both of MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/343,867

(22) Filed: Jun. 30, 1999

Related U.S. Application Data

(63) Continuation of application No. 06/917,925, filed on Oct. 10, 1986, now Pat. No. 5,959,091, which is a continuation-in-part of application No. 06/679,849, filed on Dec. 10, 1984, now abandoned.

(51) Int. Cl.[7] .............................. A61K 38/00; C07K 1/00

(52) U.S. Cl. .............................................. 514/12; 530/350

(58) Field of Search .............................. 514/12; 530/350; 435/320.1, 252.3; 536/23.71

(56) References Cited

U.S. PATENT DOCUMENTS

| | | | |
|---|---|---|---|
| 4,277,564 | 7/1981 | Johnson | 435/242 |
| 4,374,200 | 2/1983 | Olsen | 435/172 |
| 4,448,885 | 5/1984 | Schnepf et al. | 435/253 |
| 4,467,036 | 8/1984 | Schnepf et al. | 435/320.1 |
| 4,536,475 | 8/1985 | Anderson | 435/172.3 |
| 4,666,848 | 5/1987 | Gefland et al. | 435/253 |
| 5,928,891 | 7/1999 | Klier et al. | 435/69.1 |

FOREIGN PATENT DOCUMENTS

| | | |
|---|---|---|
| 0093062 | 11/1983 | (EP) . |
| 0164245 | 12/1985 | (EP) . |
| WO86/01536 | 3/1986 | (WO) . |

OTHER PUBLICATIONS

Aronson et al. Journal of Bacteriology 151(1):399–410, Jul. 1982.*

Whiteley, et al. "Cloning the Crystal Protein Gene of *B.t.* in *E. coli" Molecular Cloning and Gene Regulation in Bacilli,* Academic Press (1982) pp. 131–144.

Klier, A., Fargette, F., Ribier, J. and Rapoport, G., (1982) *EMBO J.,* 1:791–799.

Held, G. A., Bulla, L. A., Ferrari, E., Aronson, A. I. and Minnich, S.A., (1982) *Proc. Natl. Acad. Sci. USA,* 79:6065–6069.

Wong, H. C., Schnepf, H.E. and Whiteley, H. R., (1983) *J Bio. Chem.,* 258:1960–1967.

Whiteley et al., "Structural and Regulatory Analysis of a Cloned *Bacillus thuringiensis* Chrystal Protein Gene", *Genetics and Biotechnology* of Bacilli, Academic Press (1984) pp. 375–386.

Kronstad, et al., *J. of Bacteriology,* (April 1983) pp. 419–428.

Bulla, et al. (1981) *J. of Biol. Chem.,* 256:3000–3004.

(List continued on next page.)

*Primary Examiner*—Christopher S. F. Low
*Assistant Examiner*—Devesh Srivastava
(74) *Attorney, Agent, or Firm*—Timothy K. Ball, Esq.; Howrey Simon Arnold & White, LLP

(57) ABSTRACT

The invention relates to genetically engineered plant-colonizing microorganisms which proliferate in symbiotic or non-detrimental relationships with the plant in the plant environment. Such microorganisms contain DNA derived from *Bacillus thuringiensis* which codes for the insecticidal crystal protein toxin. The engineered plant-colonizing microorganisms of the invention and their progency are active against a variety of lepidopterous pests. The invention further relates to the use of such plant-colonizing microorganisms in a method of killing or inhibiting lepidopterous pests and to insecticidal compositions containing the plant-colonizing microorganism as the active insecticidal agent.

8 Claims, 13 Drawing Sheets

OTHER PUBLICATIONS

Nagamatsu, et al. (2984) *Agric. Biol. Chem.,* 48:611–619.

Dean, D. H. (1984) *Biotechnology and Genetic Engineering Reviews,* 2:341–363.

Faust et al. (1981) *Genetic Engineering in the Plant Sciences,* pp. 225–253, Praeger Publishers, New York.

Gray et al. (Feb. 1984) *Bio/Technology,* pp. 161–165.

Maniatis et al. In *Molecular Cloning, A Laboratory Manual,* Cold Spring Harbor Laboratory, 1982, pp. 405–406.

Mergeay et al. (1978) *Journal of Bacteriology* 136:1187–1188.

Schnepf et al. (1981) *Proc. Natl. Acad. Sci. USA,* 78:2893–2897.

Schnepf, H. et al., Delineation of a Toxin–encoding Segment of a *Bacillus thuringiensis* Crystal Protein Gene, *The Journal of Biological Chemistry* 260:6373–6280 (1985).

Thorne, L. et al., Structural Similarity between the Lepidoptera– and Diptera–Specific Insecticidal Endotoxin Genes of *Bacillus thuringiensis* subsp. *"kurstaki"* and *"israelensis", Journal of Bacteriology* 166:801–811 (1986).

Honigman, A. et al., Cloning and expression of the lepidopteran toxin produced by *Bacillus thuringiensis* var. *thruingiensis* in *Escherichia coli, Gene* 42:69–77 (1986).

* cited by examiner

| Recombinant Plasmid | Restriction Sites of Inserted B.t. Fragment | Fragment Size (Kb) |
|---|---|---|
| pMAP8 | B  H  K  H  K  B <br>                 N  S | 4.6 |
| pMAP10 | B    2.4 Kb    K    1.5 Kb    K    B | 3.1 |
| pMAP11 | B    3.0 Kb    N   .5 Kb   S    B | 4.1 |

B = BamHI
H = Hind III
K = Kpn I
N = Nru I
S = ScaI

```
                                   -150              -130
          BemHI       .PstI         .        .         .
          GGATCCGTCGACCTGCAGGAACACCCTGGGTCAAAAATTGATATTTAGTAA
          ├─pUC7─────┤ PetI ┼────── B.t. Toxin Gene ──────→
                            linker

        -110                -90               -70
     .        .        .        .        .        .
     AATTAGTTGCACTTTGTGCATTTTTTCATAAGATGAGTCATATGTTTTAAATTGTAGTAA

         -50                -30               -10
     .        .        .        .        .        .
     TGAAAAACAGTATTATATCATAATGAATTGGTATCTTAATAAAAGAGATGGAGGTAACTT

          10                 30                50
             .        .        .        .        .        .
     ATGGATAACAATCCGAACATCAATGAATGCATTCCTTATAATTGTTTAAGTAACCCTGAA
     MetAspAsnAsnProAsnIleAsnGluCysIleProTyrAsnCysLeuSerAsnProGlu

          70                 90               110
             .        .        .        .        .        .
     GTAGAAGTATTAGGTGGAGAAAGAATAGAAACTGGTTACACCCCAATCGATATTTCCTTG
     ValGluValLeuGlyGlyGluArgIleGluThrGlyTyrThrProIleAspIleSerLeu

         130                150               170
             .        .        .        .        .        .
     TCGCTAACGCAATTTCTTTTGAGTGAATTTGTTCCCGGTGCTGGATTTGTGTTAGGACTA
     SerLeuThrGlnPheLeuLeuSerGluPheValProGlyAlaGlyPheValLeuGlyLeu
```

FIG. 3A

```
        190                 210                 230
         .         .         .         .         .         .
GTTGATATAATATGGGGAATTTTTGGTCCCTCTCAATGGGACGCATTTCTTGTACAAATT
ValAspIleIleTrpGlyIlePheGlyProSerGlnTrpAspAlaPheLeuValGlnIle

        250                 270                 290
         .         .         .         .         .         .
GAACAGTTAATTAACCAAAGAATAGAAGAATTCGCTAGGAACCAAGCCATTTCTAGATTA
GluGlnLeuIleAsnGlnArgIleGluGluPheAlaArgAsnGlnAlaIleSerArgLeu

        310                 330                 350
         .         .         .         .         .         .
GAAGGACTAAGCAATCTTTATCAAATTTACGCAGAATCTTTTAGAGAGTGGGAAGCAGAT
GluGlyLeuSerAsnLeuTyrGlnIleTyrAlaGluSerPheArgGluTrpGluAlaAsp

        370                 390                 410
         .         .         .         .         .         .
CCTACTAATCCAGCATTAAGAGAAGAGATGCGTATTCAATTCAATGACATGAACAGTGCC
ProThrAsnProAlaLeuArgGluGluMetArgIleGlnPheAsnAspMetAsnSerAla

        430                 450                 470
         .         .         .         .         .         .
CTTACAACCGCTATTCCTCTTTTTGCAGTTCAAAATTATCAAGTTCCTCTTTTATCAGTA
LeuThrThrAlaIleProLeuPheAlaValGlnAsnTyrGlnValProLeuLeuSerVal

        490                 510                 530
         .         .         .         .         .         .
TATGTTCAAGCTGCAAATTTACATTTATCAGTTTTGAGAGATGTTTCAGTGTTTGGACAA
TyrValGlnAlaAlaAsnLeuHisLeuSerValLeuArgAspValSerValPheGlyGln
```

FIG. 3B

```
     550          570          590
      .     .     .     .     .     .
AGGTGGGGATTTGATGCCGCGACTATCAATAGTCGTTATAATGATTTAACTAGGCTTATT
ArgTrpGlyPheAspAlaAlaThrIleAsnSerArgTyrAsnAspLeuThrArgLeuIle

     610          630          650
      .     .     .     .     .     .
GGCAACTATACAGATCATGCTGTACGCTGGTACAATACGGGATTAGAGCGTGTATGGGGA
GlyAsnTyrThrAspHisAlaValArgTrpTyrAsnThrGlyLeuGluArgValTrpGly

     670          690          710
      .     .     .     .     .     .
CCGGATTCTAGAGATTGGATAAGATATAATCAATTTAGAAGAGAATTAACACTAACTGTA
ProAspSerArgAspTrpIleArgTyrAsnGlnPheArgArgGluLeuThrLeuThrVal

     730          750          770
      .     .     .     .     .     .
TTAGATATCGTTTCTCTATTTCCGAACTATGATAGTAGAACGTATCCAATTCGAACAGTT
LeuAspIleValSerLeuPheProAsnTyrAspSerArgThrTyrProIleArgThrVal

     790          810          830
      .     .     .     .     .     .
TCCCAATTAACAAGAGAAATTTATACAAACCCAGTATTAGAAAATTTTGATGGTAGTTTT
SerGlnLeuThrArgGluIleTyrThrAsnProValLeuGluAsnPheAspGlySerPhe

     850          870          890
      .     .     .     .     .     .
CGAGGCTCGGCTCAGGGCATAGAAGGAAGTATTAGGAGTCCACATTTGATGGATATACTT
ArgGlySerAlaGlnGlyIleGluGlySerIleArgSerProHisLeuMetAspIleLeu
```

FIG. 3C

```
        910                930                950
          .         .         .         .         .         .
AATAGTATAACCATCTATACGGATGCTCATAGAGGAGAATATTATTGGTCAGGGCATCAA
AsnSerIleThrIleTyrThrAspAlaHisArgGlyGluTyrTyrTrpSerGlyHisGln

        970                990               1010
          .         .         .         .         .         .
ATAATGGCTTCTCCTGTAGGGTTTTCGGGGCCAGAATTCACTTTTCCGCTATATGGAACT
IleMetAlaSerProValGlyPheSerGlyProGluPheThrPheProLeuTyrGlyThr

       1030               1050               1070
          .         .         .         .         .         .
ATGGGAAATGCAGCTCCACAACAACGTATTGTTGCTCAACTAGGTCAGGGCGTGTATAGA
MetGlyAsnAlaAlaProGlnGlnArgIleValAlaGlnLeuGlyGlnGlyValTyrArg

       1090               1110               1130
          .         .         .         .         .         .
ACATTATCGTCCACCTTATATAGAAGACCTTTTAATATAGGGATAAATAATCAACAACTA
ThrLeuSerSerThrLeuTyrArgArgProPheAsnIleGlyIleAsnAsnGlnGlnLeu

       1150               1170               1190
          .         .         .         .         .         .
TCTGTTCTTGACGGGACAGAATTTGCTTATGGAACCTCCTCAAATTTGCCATCCGCTGTA
SerValLeuAspGlyThrGluPheAlaTyrGlyThrSerSerAsnLeuProSerAlaVal

       1210               1230               1250
          .         .         .         .         .         .
TACAGAAAAAGCGGAACGGTAGATTCGCTGGATGAAATACCGCCACAGAATAACAACGTG
TyrArgLysSerGlyThrValAspSerLeuAspGluIleProProGlnAsnAsnAsnVal
```

FIG. 3D

```
     1270                1290                1310
      .         .         .         .         .         .
CCACCTAGGCAAGGATTTAGTCATCGATTAAGCCATGTTTCAATGTTTCGTTCAGGCTTT
ProProArgGlnGlyPheSerHisArgLeuSerHisValSerMetPheArgSerGlyPhe

     1330                1350                1370
      .         .         .         .         .         .
AGTAATAGTAGTGTAAGTATAATAAGAGCTCCTATGTTCTCTTGGATACATCGTAGTGCT
SerAsnSerSerValSerIleIleArgAlaProMetPheSerTrpIleHisArgSerAla

     1390                1410                1430
      .         .         .         .         .         .
GAATTTAATAATATAATTCCTTCATCACAAATTACACAAATACCTTTAACAAAATCTACT
GluPheAsnAsnIleIleProSerSerGlnIleThrGlnIleProLeuThrLysSerThr

     1450                1470                1490
      .         .         .         .         .         .
AATCTTGGCTCTGGAACTTCTGTCGTTAAAGGACCAGGATTTACAGGAGGAGATATTCTT
AsnLeuGlySerGlyThrSerValValLysGlyProGlyPheThrGlyGlyAspIleLeu

     1510                1530                1550
      .         .         .         .         .         .
CGAAGAACTTCACCTGGCCAGATTTCAACCTTAAGAGTAAATATTACTGCACCATTATCA
ArgArgThrSerProGlyGlnIleSerThrLeuArgValAsnIleThrAlaProLeuSer

     1570                1590                1610
      .         .         .         .         .         .
CAAAGATATCGGGTAAGAATTCGCTACGCTTCTACCACAAATTTACAATTCCATACATCA
GlnArgTyrArgValArgIleArgTyrAlaSerThrThrAsnLeuGlnPheHisThrSer
```

FIG. 3E

```
        1630                1650                1670
          .         .         .         .         .         .
ATTGACGGAAGACCTATTAATCAGGGGAATTTTTCAGCAACTATGAGTAGTGGGAGTAAT
IleAspGlyArgProIleAsnGlnGlyAsnPheSerAlaThrMetSerSerGlySerAsn

        1690                1710                1730
          . HindIII .         .         .         .         .
TTACAGTCCGGAAGCTTTAGGACTGTAGGTTTTACTACTCCGTTTAACTTTTCAAATGGA
LeuGlnSerGlySerPheArgThrValGlyPheThrThrProPheAsnPheSerAsnGly

        1750                1770                1790
          .         .         .         .         .         .
TCAAGTGTATTTACGTTAAGTGCTCATGTCTTCAATTCAGGCAATGAAGTTTATATAGAT
SerSerValPheThrLeuSerAlaHisValPheAsnSerGlyAsnGluValTyrIleAsp

        1810                1830                1850
          .         .         .         .         .         .
CGAATTGAATTTGTTCCGGCAGAAGTAACCTTTGAGGCAGAATATGATTTAGAAAGAGCA
ArgIleGluPheValProAlaGluValThrPheGluAlaGluTyrAspLeuGluArgAla

        1870                1890                1910
          .         .         .         .         .         .
CAAAAGGCGGTGAATGAGCTGTTTACTTCTTCCAATCAAATCGGGTTAAAAACAGATGTG
GlnLysAlaValAsnGluLeuPheThrSerSerAsnGlnIleGlyLeuLysThrAspVal

        1930                1950                1970
          .         .         .         .         .         .
ACGGATTATCATATTGATCAAGTATCCAATTTAGTTGAGTGTTTATCTGATGAATTTTGT
ThrAspTyrHisIleAspGlnValSerAsnLeuValGluCysLeuSerAspGluPheCys
```

FIG. 3F 1990 2010 2030

CTGGATGAAAAAAAAGAATTGTCCGAGAAAGTCAAACATGCGAAGCGACTTAGTGATGAG
LeuAspGluLysLysGluLeuSerGluLysValLysHisAlaLysArgLeuSerAspGlu 2050 2070 2090

CGGAATTTACTTCAAGATCCAAACTTTAGAGGGATCAATAGACAACTAGACCGTGGCTGG
ArgAsnLeuLeuGlnAspProAsnPheArgGlyIleAsnArgGlnLeuAspArgGlyTrp 2110 2130 2150

AGAGGAAGTACGGATATTACCATCCAAGGAGGCGATGACGTATTCAAAGAGAATTACGTT
ArgGlySerThrAspIleThrIleGlnGlyGlyAspAspValPheLysGluAsnTyrVal 2170 2190 2210

KpnI
ACGCTATTGGGTACCTTTGATGAGTGCTATCCAACGTATTTATATCAAAAAATAGATGAG
ThrLeuLeuGlyThrPheAspGluCysTyrProThrTyrLeuTyrGlnLysIleAspGlu 2230 2250 2270

TCGAAATTAAAAGCCTATACCCGTTACCAATTAAGAGGGTATATCGAAGATAGTCAAGAC
SerLysLeuLysAlaTyrThrArgTyrGlnLeuArgGlyTyrIleGluAspSerGlnAsp 2290 2310 2330

TTAGAAATCTATTTAATTCGCTACAATGCCAAACACGAAACAGTAAATGTGCCAGGTACG
LeuGluIleTyrLeuIleArgTyrAsnAlaLysHisGluThrValAsnValProGlyThr

FIG. 3G

```
        2350                2370                2390
          .         .         .         .         .         .
GGTTCCTTATGGCCGCTTTCAGCCCCAAGTCCAATCGGAAAATGTGCCCATCATTCCCAT
GlySerLeuTrpProLeuSerAlaProSerProIleGlyLysCysAlaHisHisSerHis

        2410                2430                2450
          .         .         .         .         .         .
CATTTCTCCTTGGACATTGATGTTGGATGTACAGACTTAAATGAGGACTTAGGTGTATGG
HisPheSerLeuAspIleAspValGlyCysThrAspLeuAsnGluAspLeuGlyValTrp

        2470                2490                2510
          .         .         .         .         .         .
GTGATATTCAAGATTAAGACGCAAGATGGCCATGAAAGACTAGGAAATCTAGAATTTCTC
ValIlePheLysIleLysThrGlnAspGlyHisGluArgLeuGlyAsnLeuGluPheLeu

        2530                2550                2570
          .         .         .         .         .         .
GAAGGAAGAGCACCATTAGTAGGAGAAGCACTAGCTCGTGTGAAAAGAGCGGAGAAAAAA
GluGlyArgAlaProLeuValGlyGluAlaLeuAlaArgValLysArgAlaGluLysLys

        2590                2610                2630
          .         .         .         .         .         .
TGGAGAGACAAACGTGAAAAATTGGAATGGGAAACAAATATTGTTTATAAAGAGGCAAAA
TrpArgAspLysArgGluLysLeuGluTrpGluThrAsnIleValTyrLysGluAlaLys

        2650                2670                2690
          .         .         .         .         .         .
GAATCTGTAGATGCTTTATTTGTAAACTCTCAATATGATAGATTACAAGCGGATACCAAC
GluSerValAspAlaLeuPheValAsnSerGlnTyrAspArgLeuGlnAlaAspThrAsn
```

FIG. 3H

```
    2710                2730                2750
  NruI  .         .         .         .    HindIII    .
ATCGCGATGATTCATGCGGCAGATAAACGCGTTCATAGCATTCGAGAAGCTTATCTGCCT
IleAlaMetIleHisAlaAlaAspLysArgValHisSerIleArgGluAlaTyrLeuPro

    2770                2790                2810
         .         .         .         .         .         .
GAGCTGTCTGTGATTCCGGGTGTCAATGCGGCTATTTTTGAAGAATTAGAAGGGCGTATT
GluLeuSerValIleProGlyValAsnAlaAlaIlePheGluGluLeuGluGlyArgIle

    2830                2850                2870
         .         .         .         .         .         .
TTCACTGCATTCTCCCTATATGATGCGAGAAATGTCATTAAAAATGGTGATTTTAATAAT
PheThrAlaPheSerLeuTyrAspAlaArgAsnValIleLysAsnGlyAspPheAsnAsn

    2890                2910                2930
         .         .         .         .         .         .
GGCTTATCCTGCTGGAACGTGAAAGGGCATGTAGATGTAGAAGAACAAAACAACCACCGT
GlyLeuSerCysTrpAsnValLysGlyHisValAspValGluGluGlnAsnAsnHisArg

    2950                2970                2990
         .         .         .         .         .         .
TCGGTCCTTGTTGTTCCGGAATGGGAAGCAGAAGTGTCACAAGAAGTTCGTGTCTGTCCG
SerValLeuValValProGluTrpGluAlaGluValSerGlnGluValArgValCysPro

    3010                3030                3050
         .         .         .         .         .         .
GGTCGTGGCTATATCCTTCGTGTCACAGCGTACAAGGAGGGATATGGAGAAGGTTGCGTA
GlyArgGlyTyrIleLeuArgValThrAlaTyrLysGluGlyTyrGlyGluGlyCysVal
```

FIG. 3I 3070 3090 3110

ACCATTCATGAGATCGAGAACAATACAGACGAACTGAAGTTTAGCAACTGTGTAGAAGAG
ThrIleHisGluIleGluAsnAsnThrAspGluLeuLysPheSerAsnCysValGluGlu 3130 3150 3170

GAAGTATATCCAAACAACACGGTAACGTGTAATGATTATACTGCGACTCAAGAAGAATAT
GluValTyrProAsnAsnThrValThrCysAsnAspTyrThrAlaThrGlnGluGluTyr 3190 3210 3230

GAGGGTACGTACACTTCTCGTAATCGAGGATATGACGGAGCCTATGAAAGCAATTCTTCT
GluGlyThrTyrThrSerArgAsnArgGlyTyrAspGlyAlaTyrGluSerAsnSerSer 3250 3270 3290

GTACCAGCTGATTATGCATCAGCCTATGAAGAAAAAGCATATACAGATGGACGAAGAGAC
ValProAlaAspTyrAlaSerAlaTyrGluGluLysAlaTyrThrAspGlyArgArgAsp 3310 3330 3350

AATCCTTGTGAATCTAACAGAGGATATGGGGATTACACACCACTACCAGCTGGCTATGTG
AsnProCysGluSerAsnArgGlyTyrGlyAspTyrThrProLeuProAlaGlyTyrVal 3370 3390 3410

ScaI

ACAAAAGAATTAGAGTACTTCCCAGAAACCGATAAGGTATGGATTGAGATCGGAGAAACG
ThrLysGluLeuGluTyrPheProGluThrAspLysValTrpIleGluIleGlyGluThr

FIG. 3J

```
       3430                3450                3470
          .         .         .         .         .         .
GAAGGAACATTCATCGTGGACAGCGTGGAATTACTTCTTATGGAGGAATAATATATGCTT
GluGlyThrPheIleValAspSerValGluLeuLeuLeuMetGluGluEnd

       3490                3510                3530
          .         .         .         .         .         .
TAAAATGTAAGGTGTGCAAATAAAGAATGATTACTGACTTGTATTGACAGATAAATAAGG

       3550                3570                3590
          .         .         .         .         .         .
AAATTTTTATATGAATAAAAAACGGGCATCACTCTTAAAAGAATGATGTCCGTTTTTTGT

       3610                3630                3650
          .         .         .         .         .  KpnI .
ATGATTTAACGAGTGATATTTAAATGTTTTTTTGCGAAGGCTTTACTTAACGGGGTACC
```

FIG. 3K

INSERTION OF THE *BACILLUS THURINGIENSIS* CRYSTAL PROTEIN GENE INTO PLANT COLONIZING MICROORGANISMS AND THEIR USE

This application is a continuation of application Ser. No. 06/917,925 filed Oct. 10, 1986, (now U.S. Pat. No. 5,959, 091) which is a continuation-in-part application of application Ser. No. 06/679,849, filed Dec. 10, 1984 (now abandoned).

BACKGROUND OF THE INVENTION

The present invention is directed to a plant-colonizing microorganism, which has been engineered to contain heterologous DNA coding for a high molecular weight protein having insecticidal activity against lepidopterous larvae. The invention is also directed to insecticidal compositions containing such microorganisms as the active agent and to the use of such plant-colonizing microorganisms in a method of combatting lepidopterous pests.

*Bacillus thuringiensis* is a spore forming soil bacterium which is known for its ability to produce a parasporal crystal which is lethal to a wide variety of lepidopteran larvae. The crystals, which account for 20–30% of the dry weight of sporulated cultures, are composed primarily of a single, high molecular weight protein (134,000 daltons) which is synthesized only during sporulation.

Whiteley et al (1) reported the isolation of plasmid DNA from *Bacillus thuringiensis var. kurstaki* HD-1, insertion of said DNA into the cloning vector pBR322 and transformation into *Escherichia coli* strain HB101. Colonies presumed to contain recombinant plasmids were screened for production of an antigen that would react with an antibody made against *B. thuringiensis* crystal protein toxin. One recombinant strain, identified as ES12, was isolated which synthesized a polypeptide of 130,000 daltons which reacted with antibody directed to the crystal protein. Protein extracts of ES12 were toxic to larvae of the tobacco hornworm, *Manduca sexta*. The amounts of polypeptide produced were very low compared to those that can be produced by *B. thuringiensis*. This appeared to be due to the different methods of regulation of protein production in *B. thuringiensis* and *E. coli.*

Klier et al (2) reported that the crystal protein gene of *Bacillus thuringiensis* strain berliner 1715 occurred on both a large host plasmid and on the chromosomal DNA. A DNA sequence corresponding to the chromosomal sequence was inserted into plasmid pBT 15–88. The inserted sequence of pBT 15–88 was not expressed in *E. coli.* A 14 Kb BamHI DNA fragment from the 42 megadalton host plasmid was cloned into the BamHI site of pHV33 and this vector was inserted into *E. coli.* Extracts of *E. coli* containing the recombinant plasmid were immunologically cross-reactive against antibodies directed against purified crystal protein. The polypeptide synthesized by *E. coli* containing the recombinant plasmid had approximately 10% the activity of that synthesized by sporulating cells of *B. thuringiensis*. Five-fold concentrated extract of *E. coli* harboring the recombinant plasmid when spread on cabbage leaves and fed ad libitum were toxic to the larvae of *Pierris brassica*. Klier also inserted pHV33 containing the 14 Kb insert into *B. subtilis*. The crystal protein gene was not expressed in vegetative cells of *B. subtilis* although it was expressed in sporulating cells, the amount of crystal protein produced by the sporulating cells was about 10% of that produced by sporulating *B. thuringiensis.*

Held et al (3) obtained DNA fragments of *B. thuringiensis var. kurstaki* by EcoRI digestion and cloned these fragments into the vector Charon 4A. *E. coli* were infected with a recombinant bacteriophage, C4R6C, consisting of cloning vector Charon 4A and DNA from *B. thuringiensis*. These infected cells produced protoxin antigen which was the same size as the *B. thuringiensis* protoxin and protein extracts were toxic to neonate larvae of *Manduca sexta*. Hybridization of C4K6C DNA to *B. thuringiensis* plasmids indicated that the original Charon 4A clone contained the genes of chromosomal, not plasmid origin.

Wong et al (4) reported the nucleotide sequence of the promoter region and part of the coding region of the crystal protein gene from *B. thuringiensis var. kurstaki* HD-1-Dipel. A potential ribosome binding site of 11 nucleotides was located three nucleotides upstream from the initiator ATG codon. The deduced sequence for the first 333 amino acids of the crystal protein was reported.

U.S. Pat. No. 4,448,885 describes plasmids capable of replicating in an *E. coli* bacterial host species which contains expressible heterologous DNA coding for a polypeptide of 130,000 daltons which has the immunological properties of the crystal protein of *B. thuringiensis*. Also disclosed is an *E. coli* bacterial strain transformed to express a polypeptide of 130,000 daltons which reportedly has immunological properties of the crystal protein of *B. thuringiensis*. A method of using said bacterial strains to produce an insecticidal effect is also disclosed.

Commercial insecticidal preparations containing spores and crystalline protein produced by *Bacillus thuringiensis* are available as wettable powders and aqueous suspensions under such names as Dipel® and Thuricide®. These materials are used for the control of lepidopteran larvae such as Spruce budworm, cabbage looper, imported cabbage worm, gypsy moth, etc., which prey upon tobacco, cotton, soybeans, etc.

Significant limitations to the use of commercial preparations of crystalline endotoxin of *Bacillus thuringiensis* include the need for repeated applications of the insecticidal preparations and limitation of the insect target range. Another disadvantage is that the crystal protein is only produced during the sporulation stage of the *B. thuringiensis* life cycle. Such a growth phase limitation, particularly in an industrial process, can result in inconvenience and excessive time requirements during manufacture. At the completion of sporulation, the self-lysing cells release both spores and crystals into the culture medium. Because of environmental concerns it is desirable that commercial insecticidal preparations be substantially free of spores. However, because of the similarity in size and density of the spores and crystal protein toxin, separation of the crystals from the spores is complicated and laborious and thus, costly. Further, pressures resulting from growth phase limitations or other factors may result in strains of *B. thuringiensis* losing their ability to produce the crystals; such acrystalliferous strains do not have insecticidal activity.

Although the isolation of DNA from *B. thuringiensis* coding for the crystal protein toxin and the insertion of this DNA into expression vectors for the transformation of *E. coli* or *B. subtilis* is known, the prior art does not teach that such DNA can be inserted into plant-colonizing microorganisms, that such DNA will be expressed and that the plant-colonizing microorganism will have insecticidal activity against lepidopteran pests. Nor does the art teach that such plant-colonizing microorganisms can live and grow in the "plant environment" and give contact or systemic season long insect control avoiding the need for repeated applications of the insecticidal crystal protein. The delivery of insecticidal protein via a genetically engineered plant-colonizing microorganism which colonizes the "plant environment" and which expresses the insecticidal protein in the plant environment, i.e., on the leaf, stem, stalk, floral parts or root surface is unexpected in view of the prior art which is directed to the production of insecticidal crystal protein in culture.

The insecticidally active genetically engineered plant-colonizing microorganisms of the present invention thus provide a superior methods of combatting certain lepidopterous insects which avoids the problems associated with the use of conventional chemical insecticides and which avoids the problems and expense related to the production of the insecticidally active protein in culture and separation and purification of the insecticidal protein from the culture medium.

SUMMARY OF THE INVENTION

The invention relates to genetically engineered plant-colonizing microorganisms which proliferate in symbiotic or non-detrimental relationships with the plant in the plant environment. Such microorganisms contain DNA derived from *Bacillus thuringiensis* which codes for the insecticidal crystal protein toxin. The engineered plant-colonizing microorganisms of the invention and their progeny are active against a variety of lepidopterous pests. The invention further relates to the use of such plant-colonizing microorganisms in a method of killing or inhibiting lepidopterous pests and to insecticidal compositions containing the plant-colonizing microorganism as the active insecticidal agent.

BRIEF DESCRIPTION OF THE DRAWINGS

Following is a brief description of the drawings which are not drawn to scale but are illustrative of materials which may be used in practicing the invention.

FIGS. 3A to 3K illustrates the DNA sequence and derived amino acid sequence of the protein toxin encoded by plasmid pMAP4.

DETAILED DESCRIPTION OF THE INVENTION

Figure 1:
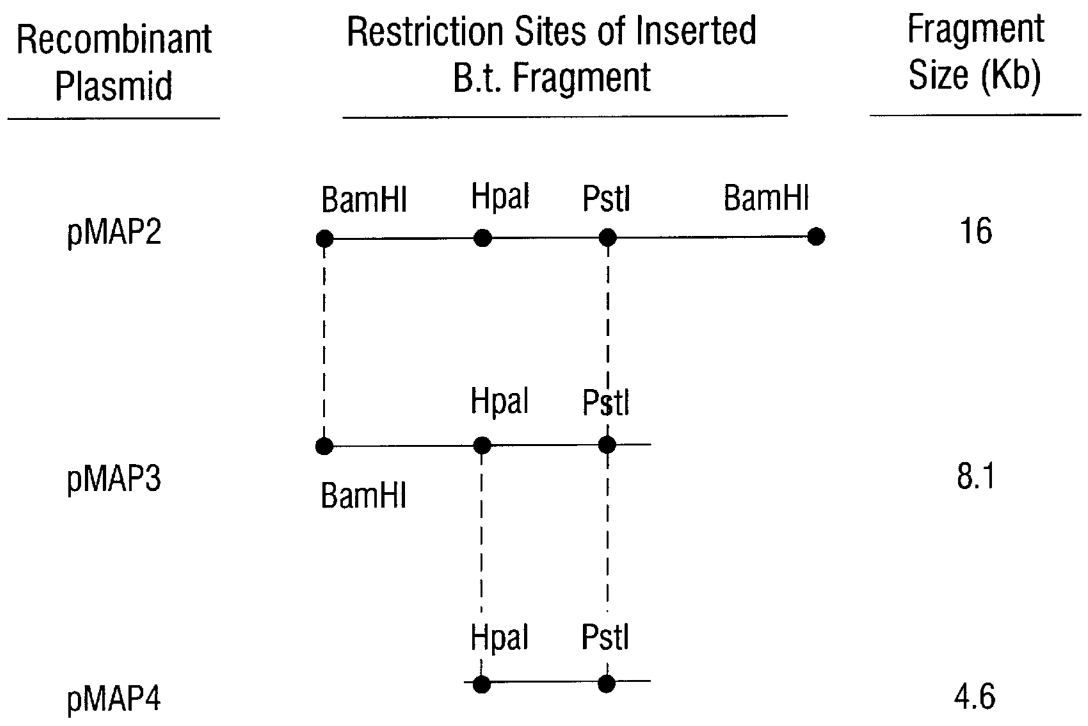
FIG. 1 is a restriction endonuclease cleavage map of the inserted *B. t.* fragment of pMAP2, pMAP3 and pMAP4.

The present invention is directed to a genetically engineered plant-colonizing microorganism containing heterologous DNA which expresses a protein having insecticidal activity and having substantially the immunological properties of the crystal protein toxin of *Bacillus thuringiensis*. The invention further relates to the use of such plant-colonizing microorganisms in a method of inhibiting the growth and development of lepidopterous pests and to insecticidal compositions containing these plant-colonizing microorganisms as the active insecticidal agent.

As used herein, the term "plant-colonizing microorganism" refers to a microorganism which is capable of colonizing the "plant environment" and which can express the insecticidal protein in the "plant environment". The plant associated microorganism is one which can exist in symbiotic or non-detrimental relationship with the plant in the "plant environment". As used herein, the term "plant-colonizing microorganism" does not include spore forming organisms of the family Bacillaceae as for example, *Bacillus thuringiensis var. kurstaki, Bacillus thuringiensis var. israeliensis* and *Bacillus subtilis*.

The term "plant environment" refers to the surface of the plant, e.g., leaf, stem, stalk, floral parts or root surface and to the "rhizosphere", i.e., the soil which surrounds and which is influenced by the roots of the plant.

Exemplary of the plant-colonizing microorganisms which may be engineered as taught herein are bacteria from the genera Pseudomonas, Agrobacterium, Rhizobium, Erwinia, Azotobacter, Azospirillum, Klebsiella, Flavobacterium and Alcaligenes. Rhizosphere colonizing bacteria from the genus Pseudomonas are preferred for use herein, especially the flourescent pseudomonads, e.g., *Pseudomonas fluorescens* which is especially competitive in the plant rhizosphere and in colonizing the surface of the plant roots in large numbers. Another group of particularly suitable plant-colonizing microorganisms for use herein are those of the genus Agrobacterium; *Agrobacterium radiobacter* is particularly suitable for use herein.

As used herein, the term "heterologous DNA" refers to any DNA fragment isolated from *B. thuringiensis* which codes for a protein that is immunologically cross-reactive to the insecticidally active crystal protein toxin produced by *B. thuringiensis*. Both plasmid and chromosomal DNA, or a sub-fragmentation sequence thereof, may be used to genetically engineer the plant-colonizing microorganisms described herein. The synthetically produced equivalents may likewise be used and such use is contemplated herein. Stated another way, DNA from whatever source, which expresses an insecticidally active protein which is substantially immunologically cross-reactive with the crystal protein toxin of *B. thuringiensis* is contemplated for use in genetically engineering the plant-colonizing microorganisms described herein.

Plasmid DNA from *B. thuringiensis var. kurstaki* HD-1 was used herein as the source of the crystal protein toxin gene. This strain was obtained from Dr. T. Yamamoto of the USDA—Brownsville, Tex. There are a variety of publicly available *B. thuringiensis* strains which may likewise be used; e.g., *B. thuringiensis var. kurstaki* HD-1 (NRRL B-3792) and *B. thuringiensis var. kurstaki* HD-73 (NRRL B-4499). See also U.S. Pat. No. 4,277,564.

The plasmid DNA fragment isolated from the *B. thuringiensis* donor strain was a 16 Kb BamHI fragment which expresses protein that is immunologically cross-reactive with antibody made to the 134,000 dalton crystal protein toxin of *B. thuringiensis*. The 16 Kb BamHI fragment was subcloned to produce an 8.1 Kb BamHI-PstI fragment. This fragment was further subcloned to produce a 4.6 Kb HpaI-PstI fragment. All of these DNA fragments coded for an insecticidally active protein toxin of about 134,000 daltons in size and which was immunologically cross-reactive with antibody made to the crystal protein toxin of *B. thuringiensis*. Deletions of the 4.6 Kb fragment are contemplated for use herein to the extent that the deletions do not result in the loss of the insecticidal properties of the protein capable of being coded by the deletion fragments. DNA fragments have been made by deletion ranging from 4.1–2.4 Kb in size and coding for an insecticidally active protein of about 110,000 to about 80,000 daltons.

As would be recognized by skilled artisans, there are inherent advantages in using the smallest possible DNA fragment which will still express insecticidally active protein. For example, a higher yield of *B. t.* DNA is obtained in the cloning steps and introduction of superfluous DNA not coding for the insecticidally toxin into the genome of the plant-colonizing microorganism is reduced.

Cloning vectors used herein are known in the art and are generally available. Choice of a particular vector is within the skill of the art and is largely a matter of individual preference. Plasmid cloning vectors which may be mentioned as being suitable for use herein are identified in Table I.

TABLE I

| Plasmid Vector | Brief Description | Reference |
|---|---|---|
| pBR28 | — | Bolivar, F., (1978) Gene 4:121 |
| pUC7 | — | Vieira, J. and Messing, J. (1982) Gene 19:259 |
| pUC8 | Multi-site pBR322 (ATCC 37017) like Vector | Vieira, J. and Messing, J. (1982) Gene 19:259 |
| pMON5008 | Derivative of pKT230 | USSN 592,158 filed 3/21/84 |

The plant-colonizing microorganisms of the invention are useful in a method of combatting lepidopteran pests wherein an insecticidally effective amount of the plant-colonizing microorganism is applied to the plant environment or to the plant seed. The plant-colonizing microorganisms of the invention will have the same spectrum of insecticidal activity as the crystal protein toxin of *Bacillus thuringiensis Berliner var. kurstaki*. That is, the microorganisms of the invention are insecticidally active against such lepidopteran larvae as, for example, Spruce budworm, wax moth, cabbage looper, imported cabbage worm, gypsy moth and tobacco hornworm.

The insecticidal plant-colonizing microorganisms of the invention may be applied directly to the plant environment, e.g., to the surface of the leaves, roots or floral parts or to the plant seed. When used as a seed coating, the plant-colonizing microorganisms of the invention are applied to the plant seed prior to planting. Generally, small amounts of the insecticidally active microorganism will be required to treat such seeds.

The determination of an insecticidally effective amount of plant-colonizing microorganisms useful in the method of the invention required for a particular plant is within the skill of the art and will depend on such factors as the plant species, method of planting, and the soil type, (e.g., pH, organic matter content, moisture content).

Compositions containing the insecticidally active plant associated microorganism of the invention are prepared by formulating the biologically active microorganism with adjuvants, diluents, carriers, etc. to provide compositions in the form of finely-divided particulate solids, granules, pellets, wettable powders, dusts, aqueous suspensions, gels, dispersions, and emulsions. Illustrative of suitable carrier vehicles are: solvents e.g., water or organic solvents and finely divided solids, e.g., kaolin, chalk, calcium carbonate, talc, silicates and gypsum.

It is contemplated herein to use the insecticidal microorganisms in the methods and compositions of the invention in encapsulated form; e.g., the plant-colonizing microorganism can be encapsulated within shell walls of polymer, gelatin, lipid and the like or other formulation aids as for example emulsifiers, dispersants, surfactants, wetting agents, antifoam agents and anti-freeze agents, may be incorporated into the insecticidal compositions, especially if such compositions will be stored for any period of time prior to use.

In addition to the insecticidally active plant-colonizing microorganism the compositions of the invention may additionally contain other known biologically active agents, for example, a herbicide, fungicide, or other insecticide. Also, two or more insecticidally active plant-colonizing microorganisms may be combined.

The application of insecticidal compositions containing the genetically engineered plant-colonizing microorganisms of the invention as the active agent can be carried out by conventional techniques utilizing, for example, spreaders, power dusters, boom and hand sprayers, spray dusters and granular applicators.

The compositions of the invention are applied at an insecticidally effective amount which will vary depending on such factors as, for example, the specific lepidopteran larvae to be controlled, the specific plant to be treated and method of applying the insecticidally active compositions.

The following examples further illustrate various specific embodiments of the invention described herein. As would be apparent to skilled artisans, various changes and modifications from these examples are possible and are contemplated within the scope of the invention described here.

The insertion of heterologous DNA derived from *B. thuringiensis* coding for a high molecular weight protein having insecticidal activity into a plant-colonizing microorganism was carried out as follows:

Starting Microorganism

*Bacillus thuringiensis var. kurstaki* HD-1 utilized herein as the source of plasmid DNA for the recombinant plasmids was obtained from Dr. Takashi Yamamoto of the United States Department of Agriculture (USDA). *B. thuringiensis* strains were maintained as sporulated stock cultures according to standard procedures. Cultures were routinely monitored for crystal production by phase contrast microscopy.

Preparation of Synthetic Oligonucleotide Probes

The amino acid sequence of the crystal protein toxin gene isolated from *Bacillus thuringiensis var. kurstaki* HD-1 was partially determined according to the method of Hunkapiller et al (5). These sequences were verified using the DNA sequence of the $NH_2$-terminal portion of the crystal protein gene disclosed by Wong et al (4). Synthetic oligonucleotide sequences based on an amino acid sequence determined from the crystal protein polypeptide were prepared according to the procedure of Beaucage et al (6). The oligonucleotide probes prepared are as shown in Table II.

TABLE II

SYNTHETIC OLIGONUCLEOTIDE PROBES

| Size | Probe Seguence | Area of B.t. Protein |
|---|---|---|
| 14-mer | TGG GGA CCG GAT TC | 1200 bp region |
| 14-mer | GAA AGA ATA GAA AC | *27–31 amino acid region |
| 21-mer | CCT GAA GTA GAA-GTA TTA GGT | *19–25 amino acid region |

*numbered from $NH_2$ - terminal end

Preparation and Isolation of Plasmid DNA From *B. Thuringiensis*

Plasmid DNA from *B. thuringiensis var. kurstaki* HD-1 was purified from 1 to 2 liters of culture according to the procedure of Kronstad et al (7). All plasmid preparations were banded at least once in CsCl/ethidium bromide gradients. Plasmids 30 megadaltons and larger in size were preferentially isolated.

Digestion with restriction enzymes EcoRI, PstI, HindIII, BamHl and SmaI, was carried out according to conditions recommended by the supplier (Boehringer Mannheim). *Escherichia coli* strain JM 101 (8) and strain SR-200 (9) were used as the recipients for the transformation step. Competent cells were prepared according to standard procedures (10). Colonies transformed with plasmid pUC8, were plated on L-agar with 100 $\mu$g/ml of ampicillin and 40 $\mu$l of 4% 5-bromo-4-chloro-3-indolyl-β-D-galactopyranoside (x-gal).

Preparation of Nitrocellulose Filters and Hybridization

Plasmid DNA was transferred to nitrocellulose according to the procedure of Southern (11). Prehy-bridization was done by incubating the nitrocellulose paper with the bound transferred DNA in prehybridization fluid, 10×Denhardt's (0.2% BSA, 0.2% Ficoll, 0.2% polyvinylpyrrolidone) and 6×SSC (0.9M NaCl, 0.09M sodium citrate) for 2–4 hours at 37° C. Hybridization was done by incubating the nitrocellulose paper for 8–10 hours with 10–11 ml of the prehybridization fluid and the labelled probe. After several washes with 6×SSC at increasing temperatures (30–45° C.) the paper was exposed to X-ray film.

Cloning of the *B. t.* toxin gene in *E. coli*

BamHI-restricted pBR328 (100 ng), treated with alkaline phosphatase (Boehringer Mannheim) was mixed and ligated with 500 ng of *B. thuringiensis* plasmid DNA restricted with BamHI. $CaCl_2$ prepared competent *E. coli* SR200 were transformed and selected by ampicillin resistance and screened for tetracycline sensitivity. Analysis by mini-plasmid prep procedures (12) identified two clones which had the correct 16 Kb insert. Southern hybridization analysis with radio-labelled probes from Table II demonstrated that the DNA fragment which contained the sequence hybridizing to the synthetic probe had been sub-cloned. The two plasmids, designated pMAP1 and pMAP2, differed only in the orientation of the DNA fragment within the vector. These plasmid constructs produced material cross-reactive to *B. t.* crystal protein toxin antibody when analyzed according to Western blot procedures (13). A restriction map of the inserted *B. t.* fragment was prepared and four EcoRI (E) sites and three Hind III (H) sites were located between the BamHI (B) sites. This is schematically illustrated as:

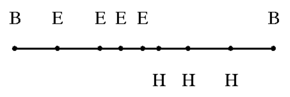

*E. coli* SR200 containing pMAP2 has been deposited in compliance with MPEP 608.01(p) with the American Type Culture Collection, 12301 Parklawn Drive, Rockville, Md. 20852 USA and has been designated ATCC #39800.

Sub-Cloning of *B. t.* Toxin

An 8.1 Kb BamHI-PstI fragment was isolated after BamHI-PstI digestion of pMAP2 by electroelution from a preparative agarose gel onto DEAE paper used according to the directions of the manufacturer Schleicher & Schuell (14). Plasmid pUC8 was used to sub-clone the BamHI-PstI fragment of pMAP2 carrying the *B. t.* gene. Ligation of pUC8 digested with BamHI and PstI with the purified 8.1 Kb BamHI-PstI fragment was followed by transformation of competent *E.coli* JM101. Transformants were selected on the basis of ampicillin resistance and a lack of β-galactosidase activity. A clone was isolated and was confirmed to contain the desired plasmid. This construct was designated pMAP3. *E. coli* JM101 containing pMAP3 has been deposited in compliance with MPEP 608.01 (p) with ATCC and has been designated ATCC #39801.

Reduction of the *B. thuringiensis* DNA insert of pMAP3 from 8.1 Kb to 4.6 Kb was done by deleting a SmaI-HpaI fragment. Plasmid pMAP3 DNA, purified by CsCl gradient centrifugation was digested with SmaI and HpaI restriction enzymes and religated. The resulting DNA fragment was utilized to transform competent *E. coli* JM101 cells. Ampicillin resistant transformants were screened by agarose electrophoresis of mini-plasmid preparations. A clone was identified which contained a plasmid with the expected DNA restriction enzyme digestion pattern. This construct was labelled pMAP4. The above-described sub-cloning of the 16 Kb insert of pMAP2 containing the *B. thuringiensis* toxin gene to an 8.1 Kb insert (pMAP3) and a 4.6 Kb insert (pMAP4) is illustrated in FIG. 1.

Insertion of DNA Isolated From *B. t.* Into Cloning Vector pMON5008

Plasmid pMON5008 constructed by B. C. Hemming and D. J. Drahos of Monsanto Company was used as a cloning vector to transform competent cells of *E. coli* with a 4.6 Kb fragment of plasmid DNA isolated from pMAP3. Plasmid pMON5008 is a derivative of plasmid pKT230; construction of pMON5008 is described in U.S. Ser. No. 592,158 filed Mar. 21, 1984, which is commonly assigned to Monsanto Company and the disclosure of which is herein incorporated by reference.

In order to get proper insertion of the 4.6 Kb fragment isolated from pMAP3 into pMON5008 adjustments to the ends of the 4.6 Kb fragment were required. A PstI linker (CCTGCAGG) was added to the 4.6Kb HpaI-PstI fragment as described below.

Plasmid pMAP3 (10 $\mu$g) was digested with HpaI; complete digestion was confirmed by agarose gel analysis. The digest was extracted with mixture of phenol/chloroform (1:1), followed by chloroform extraction and finally by ethanol extraction. The resulting precipitate was washed with TE buffer, (0.01M TRIS/0.001M EDTA, pH 8.0 and thereafter resuspended in same. Two pg of PstI linker (CCTGCAGG) obtained from New England Biolabs was combined with 2 units of T4 DNA kinase in a total volume of 10 $\mu$l of kinase/ligase buffer (11). The mixture was incubated at 37° C. for 1 hour. Thereafter, 2 $\mu$g of the Kinase/linker mixture was added to 2 $\mu$g of HpaI digested pMAP3 and 2 $\mu$l of T4 DNA ligase (2 units) and the resulting mixture was incubated for 18 hours at 22° C. after which 1 $\mu$l of 0.5M EDTA (pH 8.0) was added and the mixture was extracted as described above. The resulting precipitate was washed with TE buffer and resuspended in 90 $\mu$l of fresh TE buffer. The precipitate was digested with PstI and the digest was mixed with 6.0 $\mu$l of SM NaCl and run through a Sepharose CL-4B column. The fractions were collected and were screened by agarose gel electrophoresis. Fractions containing high molecular weight DNA were combined, precipitated, and the resulting precipitate was washed with TE buffer and thereafter resuspended in fresh TE buffer.

The DNA which was collected from the column was mixed with PstI digested plasmid vector pUC7 which had been treated with alkaline phosphatase and column-purified.

The PstI-PstI fragment was ligated into the PstI site of pUC7 and used to transform competent *E. coli* JM101. Inserting the *B. t.* gene into the unique PstI site of pUC7 positioned the gene between two BamHI sites.

Ampicillin resistant β-gal negative transformants were selected and were analyzed for the correct plasmid construct by mini-plasmid preparations and restriction endonuclease digestion. A plasmid with a 4.6 Kb fragment flanked by both PstI and BamHI sites was isolated and designated pMAP8.

Plasmid pMON5008 DNA was isolated, digested with BamHI or BglII, treated with alkaline phosphatase and purified on a Sepharose CL-4B column. A mixture of 1 μg of this vector DNA and 2 μg of pMAP8 digested with BamHI was ligated and used to transform competent *E. coli* cells. Transformants were selected by their kanamycin resistance and screened by restriction endonuclease digestion of the plasmid DNA isolated by mini-plasmid preparation. Constructs with *B. t.* DNA inserted at both the BamHI and BglII sites of pMON5008 in both orientations were obtained and identified as pMAP12, pMAP13, pMAP14 and pMAP15.

Selection of Plant-Colonizing Microorganism

*Pseudomonas fluorescens* 3732 (Ps.3732) was isolated from St. Charles, Mo. farm soil. A rifampicin resistant strain designated *Pseudomonas fluorescens* 3732-3 was identified by plating $1\times10^9$ colony forming units (CFU) on an L-agar plate with 100 μg/ml rifampicin. A nalidixic acid resistant mutant, designated Ps. 3732-3-7, was obtained by exposing to UV light $1\times10^{10}$ CFU of Ps.3732-3 in 5 ml of L-broth in an open petri plate on a gently rotating shaker. Exposure times ranged from 1 to 8 minutes and exposed colonies were plated on L-agar with 100 μg/ml of nalidixic acid. Colonies were streaked to isolation several times, grown under non-selective conditions at 30° C. in L-broth, and plated on media with and without nalidixic acid.

Engineering of Plant-Colonizing Microorganisms

Plasmids pMAP12, 13, 14 and 15 were transferred into Ps.3732-3-7 by a tri-parental mating system (16). The system consists of two donor strains and a recipient strain. The donors are two *E. coli* strains; one with the pMAP plasmid (a pMON5008 derivative with kanamycin resistance) to be transferred into Ps. 3732-3-7 and the other an *E. coli* strain with pRK2013. The transfer (tra) genes of pRK2 are located on pRK2013 and will mediate the transfer of plasmids into Ps. 3732-3-7 but will not replicate in Pseudomonads. The recipient strain is resistant to rifampicin and naladixic acid but sensitive to kanamycin.

The three strains involved in the 3-part mating system *E. coli* with pRK2013, *E. coli* with the pMON5008-derivative, and Ps.3732-3-7) were grown separately overnight in L-broth. One-tenth ml of culture was transferred to fresh L-broth and grown for three hours at 37° C. (30° C. for Ps.3732-3-7). One ml of each was pelleted by centrifugation and washed with L-broth supplemented with 0.1% glucose. All three cultures were resuspended in a total of 200 ul of L-broth and plated into the center of a freshly poured L-agar plate. The plates were incubated for 16 hours at 30° C. Cells were resuspended from the plates with 1 ml of 10 mM $MgSO_4$ and plated on Pseudomonas F (PF) agar (Difco catalogue #0448-01) with 100 ug/ml of rifampicin and 50 ug/ml of kanamycin.

Trans-conjugants were selected on PF agar with 50 μg/ml of kanamycin and 100 μg/ml of rifampicin. Desirable *P. fluorescens* 3732-3-7 colonies on PF agar were fluorescent under long wave UV light resistant to rifampicin and kanamycin resistant due to the presence of pMAP 12, 13, 14 or 15. Colonies were streaked on plates containing 64 ug/l of X-gal indicator for β-*galactosidase* to confirm the presence of this marker. *P. fluorescens* 3732-3-7 containing pMAP15 has been deposited in compliance with MPEP 608.01(p) with ATCC and is designated ATCC #39802.

Utilizing the procedure described above, *Agrobacterium radiobacter* was engineered to contain various of the novel plasmids described herein. *A. radiobacter* 212-4 containing pMAP15 has been deposited in compliance with MPEP 608.01(p) with ATCC and is designated ATCC #39803.

Preparation of Deletion Derivatives of the *B. t.* Toxin Gene

Figure 2:
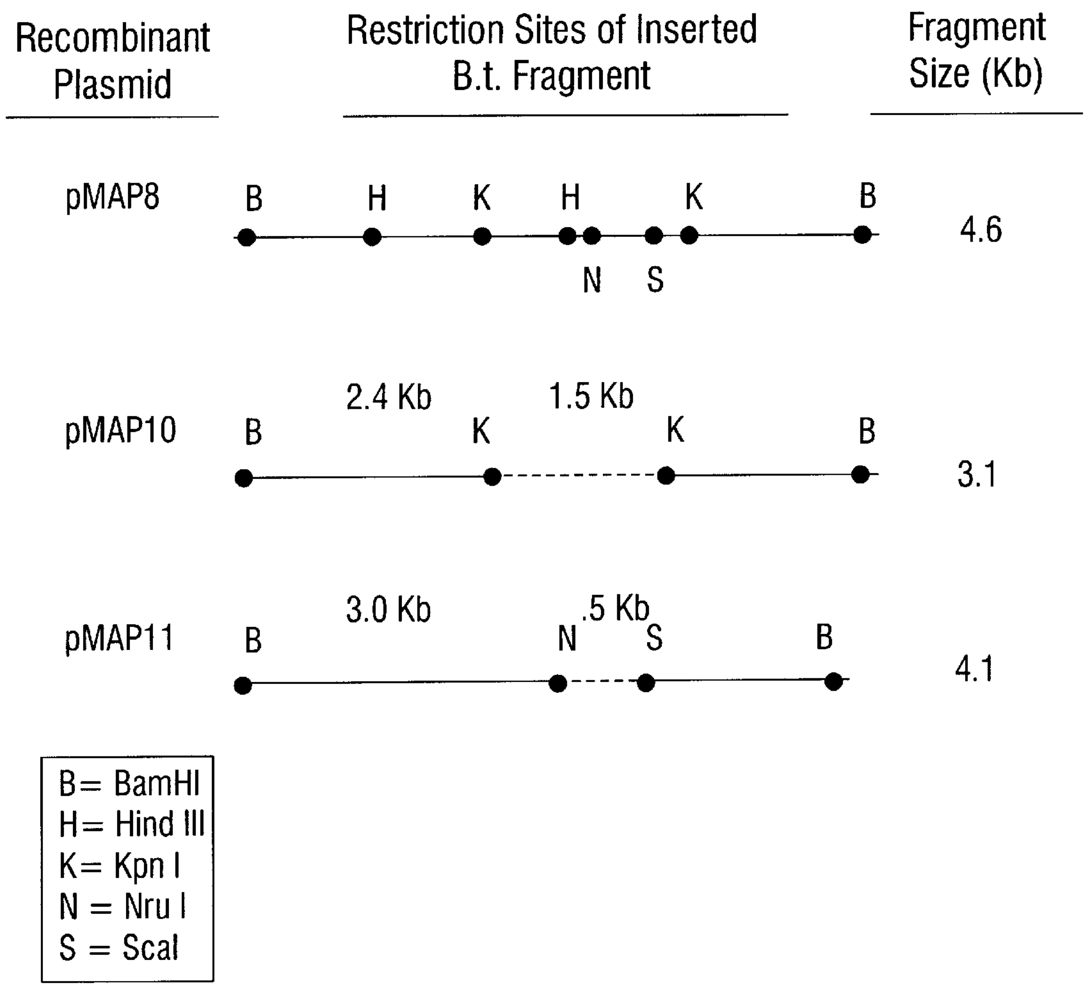
FIG. 2 is a restriction endonuclease cleavage map of the inserted *B. t.* fragment of pMAP8, pMAP10 and pMAP11.

Deletion derivatives of the *B. t.* crystal protein toxin gene were prepared by deleting DNA fragments of pMAP8 within the coding region of the 134,000 dalton toxin. Plasmid pMAP8 (1–1.5 μg in 20 uL of TE buffer was cut with the appropriate enzyme(s), extracted with a phenol/chloroform mixture (1:1), diluted to 40 uL with TE buffer, religated and used to transform $CaCl_2$—competent JM101 cells. Plasmids with deletions were identified by screening mini-prep plasmid preparations on agarose gels after electrophoresis. Two deletion derivatives, designated pMAP10 and pMAP11, were constructed by deleting a 1.4 Kb KpnI fragment (pMAP10) and a 0.5 Hb NruI-ScaI fragment (pKAP11) from pMAP8. *E. coli* with either of these constructs produced material toxic to *Manduca sexta*. The restriction map of the deletion fragments is shown in FIG. 2. The 2.4 Kb BamHI-KpnI fragment of pMAP10 was subcloned in pUC18 (18). pMAP10 and pUC18 were digested with BamHI and KpnI, mixed, ligated and used to transform *E. coli* JM101. A clone was isolated which contained a plasmid with a single 2.4 Kb BamHI-KpnI fragment. This plasmid was designated pMAP18. *E. coli* containing this plasmid were toxic to *Manduca sexta*.

Insertion of The Deletion Derivatives Into Ps. 3732-3-7

The procedure described above for the introduction of the *B. t.* gene into *Pseudomonas fluores cens* 3732-3-7 was repeated for the deleted *B. t.* DNA fragment. Plasmid DNA (pMAP10) was digested with BamHI and cloned into pMON5008 at both the BamHI and BglII sites in both orientations. These constructs were designated pMAP20, 21, 22 and 23. Immunological analysis (13) confirmed the production of CRM with anti-*B. t.* toxin antibody by *P. fluorescens* 3732-3-7.

The plant-colonizing microorganisms of the invention were tested for insecticidal activity according to the following examples. In the examples which follow, protein extracts of the plant-colonizing microorganism or unlysed whole cells were used. Protein extracts were prepared as shown in Example 1.

EXAMPLE 1

Preparation of Protein Extract

Fifty milliliters of L-broth containing 100 μg/ml ampicillin was inoculated with the microorganism (control or engineered plant-colonizing microorganism) and the inoculum was maintained overnight at 37° C. (30° C. for the pseudomonads) on a shaker. The inoculum was centrifuged for ten minutes in SS-34 10K. The pellet was resuspended in 5 ml of Ellis buffer) 0.05 M citric acid, 0.05 M $NaH_2PO_4.H_2O$, 0.05 M $Na_2CO_3$, 0.05 M 2-amino-3-methyl-1,3-propanediol, pH 10.5) 0.01 M (dithiothreitol). The suspension was quick frozen on dry ice and thereafter thawed in a water bath maintained at 30° C. Thereafter, 1 ml of glass beads (Thomas Scientific #5663 R50) was added to the suspension and the mixture vortexed for about 15 seconds. This procedure was repeated 8 times. The glass beads were removed by centrifuging through glass wool. The lysed cell sample was collected and added to an equal volume of Ellis buffer (pH 6.5). The extract was then used in the insect assay(s).

The amount of insecticidal protein expressed in several of the plant-colonizing microorganism of the invention were estimated based on ELISA (17) immunological analysis of soluble protein and Western Blot (13) analysis of total protein. Estimates for several plasmid constructs are shown in Table III.

TABLE III

| Plasmid | Plant-Colonizing Microorganism | Picograms of B.t. Protein per Microgram of Total Protein | % |
|---|---|---|---|
| pMAP12 | Ps 3732-3-7 | 816 | .08 |
| pMAP13 | " | 252 | .02 |
| pMAP14 | " | 1460 | .14 |
| pMAP15 | " | 1860 | .18 |
| pMAP15 | *P. fluorescens* 112-12 | 11584 | 1.1 |
| pMAP8 | *E. coli* JM101 | 120000 | 12 |

EXAMPLE 2

Diet Assay

A standard artificial diet medium was dispensed into 3.5×1.0 cm flat bottom wells (50 wells/tray—Flow Laboratories Inc.) to a volume of ca. 5 mls. The agar based diet hardened within a short period of time and was thereafter treated with the test (or control) material. 100 ul of test (or control) material was applied with an automatic pipettor to the surface of each of 10 wells of diet. An alcohol flamed glass spreader was used to spread the material to insure an even coating. The treated trays were allowed to dry under a vertical flow hood before placing one neonate larvae on the diet surface of each of 10 wells (10 larvae/treatment). The trays were sealed and then incubated at 28° C. for 4 days prior to evaluating the percent mortality induced by the treatment. Control treatments were included in each assay to check the effects of the diet and the un-engineered microorganism. In all cases no toxicity (i.e., mortality) was observed from the diet alone or from diet treated with non-engineered microorganisms. Table IV summarizes the results observed when microorganisms containing novel plasmids of this invention were tested for toxicity against larvae of tobacco hornworm (*Manduca sexta*), corn earworm (*Heliothi zea*) and cabbage looper (*Trichoplasia ni*).

TABLE IV

| Insect | Plasmid | Microorganism | Material Applied | % Mortality |
|---|---|---|---|---|
| Corn Earworm | pMAP1 | *E. coli* SR200 | Protein Extract | 44.4 |
| | pMAP2 | " | " | 55.5 |
| Tobacco Hornworm | pMAP1 | *E. coli* SR200 | Unlysed Cells | 100 |
| | pMAP2 | " | " | 100 |

TABLE IV-continued

| | | | | |
|---|---|---|---|---|
| | pMAP3 | *E. coli* JM101 | " | 100 |
| | pMAP4 | " | " | 100 |
| | pMAP6 | " | " | 100 |
| | pMAP7 | " | " | 100 |
| | pMAP8 | " | " | 100 |
| | pMAP12 | " | " | 100 |
| | pMAP13 | " | " | 100 |
| Tobacco Hornworm | pMAP8 | *E. coli* JM101 | Unlysed Cells | 100 |
| | pMAP12 | " | " | 100 |
| | pMAP13 | " | " | 100 |
| | pMAP14 | " | " | 100 |
| | pMAP15 | " | " | 100 |
| | pMAP12 | Ps. 3732-3-7 | " | 100 |
| | pMAP13 | " | " | 100 |
| | pMAP14 | " | " | 100 |
| | pMAP15 | " | " | 100 |
| | pMAP15 212-4 | *A. radiobacter* | " | 100 |
| Cabbage Looper | pMAP1 | *E. coli* SR200 | " | 100 |
| | | pMAP1 | " | 100 |

| Plasmid | Microorganism | Preparation | % Mortality |
|---|---|---|---|
| PMAP10 | *E. coli* | Unlysed cells | 100 |
| PMAP10 | " | " | 100 |
| PMAP11 | " | " | 100 |
| PMAP20 | " | " | 100 |
| PMAP21 | " | " | 100 |
| PMAP20 | Ps. 3732-3-7 | 100 | |
| pMAP21 | " | " | 100 |
| pMAP22 | " | " | 100 |
| pMAP23 | " | " | 100 |

EXAMPLE 3

The procedure of Example 2 was repeated except that larvae of the black cutworm (*Agrotis ipsilon*) were used. In one test no larval mortality was observed; however, application of the engineered microorganism resulted in significant weight loss of the larvae. In another test, mortality was observed. In all cases 100 p1 of protein extract or unlysed cell preparation was applied. The results are summarized in Table V.

TABLE V

| Plasmid | Microorqani8m | Preparation | % Mortality | Average Weight (mg) |
|---|---|---|---|---|
| pMAP12 | Ps. 3732-3-7 | Protein Extract | 0 | 389.6 |
| pMON5008 | " | " | 0 | 656.2 |
| — | untreated control | " | 0 | 776.4 |
| pMAP8 | *E. coli* JM 101 | Lysed Cells | 29.7 | |
| pMAP18 | " | " | 55.0 | 317.0 |
| pMAP18 | " | " | 10.0 | 255.0 |
| — | *P. fluorescens* 112-12-15 | " | 12.5 | 293.3 |
| — | untreated control | " | 0 | 290.8 |

EXAMPLE 4

Droplet Assay

A 2:1 (microbial preparation: FD&C blue dye) mix containing 10% sucrose was vortexed, then applied to the surface of a styrofoam plate in about 10 ul droplets. Neonate tobacco hornworm larvae were placed in the vicinity of the droplets and allowed to feed at will. Satiated larvae, as evidenced by their blue abdomens, were removed from the plate and placed on artificial diet. Percent mortality was evaluated after four days. The results are summarized in Table VI.

TABLE VI

| Plasmid | Microorganism | CFU/$\mu$l* | % Mortality |
|---|---|---|---|
| pMAP1 | *E. coli* SR200 | $1.0 \times 10^5$ | 50 |
| pMAP2 | " | $7.5 \times 10^4$ | 100 |
| pMAP3 | *E. coli* JM101 | $7.9 \times 10^4$ | 100 |
| pMAP4 | " | $3.4 \times 10^1$ | 100 |
| pMAP1 | *E. coli* SR200 | $8.6 \times 18^3$ | 0 |
| pMAP2 | " | $2.2 \times 10^4$ | 75 |
| pMAP4 | *E. coli* JM101 | $2.2 \times 10^4$ | 80 |

*Approximate number of Colony Forming Units ingested.

EXAMPLE 5

Leaf Disc Assay

Two (2) cm discs of tomato leaf tissue was immersed in a solution of live cells. The discs were blotted on filter paper and then the discs were added individually to wells containing distilled water moistened filter paper. The wells were identical to those used in the Diet Assay. One neonate tobacco hornworm larvae was added to each of ten wells/treatment. Mortality was recorded after 72 hours. The results are summarized in Table VIII.

TABLE VIII

| Plasmid | Microorganism | CFU/ml | % Mortality |
|---|---|---|---|
| pMAP12 | Ps. 3732-3-7 | $1 \times 10^9$ | 100 |
| pMAP15 | " | $1 \times 10^9$ | 100 |
| pMAP15 | " | $1 \times 10^9$ | 100 |
| pMAP20 | " | $1.6 \times 10^7$ | 0* |
| pMAP21 | " | $3.1 \times 10^8$ | 100 |
| pMAP22 | " | $4.0 \times 10^6$ | 0* |
| pMAP23 | " | $1.9 \times 10^7$ | 100 |

*Insects were alive; however, growth was stunted.

DNA Sequence of the *B. t.* Toxin Gene

The DNA sequence of 3734 nucleotides from pMAP4 including the entire toxin protein coding sequence was determined by the chain termination method of Sanger et al. (19). The sequence includes 75 nucleotides upstream of the translational initiation codon and extends through a KpnI site 188 nucleotides after the translational termination codon. The DNA sequence and the derived amino acid sequence for the toxin protein are shown in FIG. 3. The first nucleotide of the protein coding sequence is labeled position +1. DNA sequences from nucleotide −75 to nucleotide 220 and from nucleotide 3245 to 3650 were also determined by the chemical method of Maxam and Gilbert (20). The DNA sequence from −171 to −160 is from the known sequence of the plasmid vector pUC7 (Vieira, supra.) DNA sequence from −159 to −153 is from a chemically synthesized PstI linker (New England Biolabs); the three nucleotides from −152 to −150 are derived from the known cleavage site for restriction enzyme HpaI. The sequence from nucleotide −149 to −76 (74 nucleotides) has been inferred from known 5'-flanking sequences of other *B. t.* toxin genes (21, 22, 23, 24).

The DNA sequence of the 2.4 Kb fragment of pMAP10 begins at the BamHI site at −171 and terminates at the KpnI site at 2175. The protein toxin expressed by this truncated gene represents about 63% of the protein toxin expressed by the entire gene. *E. coli* transformants with pMAP18, which contains only the 2.4 Kb gene fragment, were toxic to *Manduca sexta* and black cutworm (Agrotis ipsilon) which data demonstrate that the shortened protein is efficacious for insect control.

Those skilled in the art recognize that certain variations of the DNA fragments and genes disclosed and claimed herein can be made by one or more nucleotide deletions, substitutions, inversions and/or additions using known techniques. It should therefore be understood that such variations which do not result in a substantial change in the activity of the protein encoded therein are considered within the scope of the present invention.

Although this invention has been described with respect to specific embodiments, the details thereof are not to be construed as limitations, for it will be apparent that various equivalents, changes and modifications may be resorted to without departing from the spirit and scope thereof and it is understood that such equivalent embodiments are to be included herein.

REFERENCES

1. Schnepf, H. E., and Whitely, H. R. (1981) Proc. Natl. Acad. Sci. USA, 78:2893–2897

2. Klier, A., Fargette, F., Ribier, J. and Rapoport, G., (1982) *EMBO J.* 1:791–799

3. Held, G. A., Bulla, L. A., Ferrari, E., Aronson, A. I. and Minnich, S. A., (1982) *Microbiology*, 79: 6065–6069. Held, G. A., et al, *Proc. Natl. Acad. Sci. USA*, 79:6065–6069

4. Wong, H. C., Schnepf, H. E., and Whiteley, H. E., (1983) *J. Biol. Chem.* 258:1960–1967

5. Hunkapiller, M. W., Hewick, R. M., Dreyer, W. J., and Hood, L. E., (1983) *Methods Enzymol*, 91:399–413

6. Beaucage, S. L. and Caruthers, M. H., (1981) Tetrahedron Lett. 22:1859–1862; see also Addams, S. P. et al, (1983) *JACS* 105:661–663

7. Kronstad, J. W., Schnepf, H. E., and Whiteley, H. R., (1983) *J. Bacteriol* 154:419–428

8. Messing, J., Crea, R. and Seeburg, P. H., (1981) *Nucleic Acids Research* 9:309–321

9. *E. coli* SR200 was obtained from Dr. S. G. Rogers of Monsanto Co., St. Louis, Mo. 63167

10. Dagert, M. and Ehrlich, S. D., (1979) *Gene* 6:23–28

11. Southern, E. M. (1975) *J. Molec. Biol.*, 98:503–517

12. *Molecular Cloning, A Laboratory Manual*, T. Maniatis, E. F. Pritsch and J. Sambrook (1982) Cold Spring Harbor, N.Y. p. 396

13. Geshoni, J. M. and Palache, G. E., (1983) Protein Blotting: Principles and Applications, *Anal Biochem* 131:1–15 or Towbin, H., Stalhelin, T. and Gordon (1979). *Proc. Natl. Acad. Sci. USA* 76:4350–4354

14. Schleicher & Schuell, Inc. Keene, N. H., 03431, USA, "Binding and Recovery of DNA and RNA Using SIS NA-45 DEAE Membrane," *Sequences-Application Update*, No. 364

15. *Molecular Cloning* (ibid) p. 396.

16. Figurski, D. H. and Helinski, D. R., (1979) *Proc. National Acad. Sci. USA* 76:1648–1652

17. *The Enzyme Linked Immunosorbent Assay, A Guide With Abstracts of Microplate Applications.* A. Voller, D. Bidwell and A. Bartlett (1979) Dynatech Laboratories, Inc., Alexandria, Va.

18. Norrander, J., Kempe, T. and Messing, J., "Insertional Vectors Using Oligonucleotide Mutagenesis," *Gene* 1983, 260(1), 101–6

19. Sanger, F., Nicklen S., and Coulson, A. R. (1977) *Proc. Nat. Acad. Sci. USA* 74:5463–5467

20. Maxam, A. M. and Gilbert, W. (1977) *Proc. Nat. Acad. Sci. USA* 74: 560–564

21. Schnepf, H. E., Wong, H. C. and Whiteley, H. R. (1985) *J. Biol. Chem.* 260: 6264–6272

22. Thorne, L., Garduno, F., Thompson, T., Decker, D., Zounes, M., Wild, M., Walfield, A. M. and Pollock, T. J. (1986) *J. Bacteriol.* 166: 801–811

23. Adang, M. J., Staver, M. J., Rocheleau, T. A., Leighton, J., Barker, R. F., and Thompson D. V., (1985) *Gene* 36: 289–300

24. Shibano, Y., Yamagata, A., Nakamura, N., Gene 34: 243–251

What is claimed is:

1. An insecticidal toxin protein of *Bacillus thuringiensis var. kurstaki* which is encoded by the 2.4 Kb Bam HI-Kpn I DNA fragment of FIG. 2.

2. A protein encoded by the DNA sequence of nucleotide 1 to 2175 of FIGS. 3A to 3K combined in the order 1–11.

3. A protein encoded by a portion of the 2.4 Kb Bam HI-Kpn I DNA fragment of FIG. 2 said protein containing fewer amino acids than the protein resulting from transcription and translation of the entire DNA fragment, wherein said protein possesses the same spectrum of insecticidal activity against lepidopteran insects as the toxin protein of *Baccillus thuringiensis var. kurstaki.*

4. An insecticidal composition comprised of:

a) one or more types of plant colonizing bacteria each of which expresses a protein of FIGS. 3A to 3K combined in the order 1–11 corresponding to about position 1 to 2175; and b) a carrier substance.

5. The composition of claim 4 wherein the carrier substance is a solid chosen from the group consisting of kaolin, chalk, calcium carbonate, talc, silicates, and gypsum.

6. The composition of claim 4 wherein the carrier substance is water or an organic solvent.

7. The composition of claim 4 wherein the plant colonizing bacteria have been encapsulated within shell walls of polymer, gelatin, or lipid.

8. The composition of claim 4 wherein the plant colonizing bacteria possesses insecticidal activity against any or all lepidopterans from the group consisting of: the Spruce budwormn, the wax moth, the cabbage looper, the imported cabbage worm, the gypsy moth, the corn earworm, the black cutworm, and the tobacco hornworm.

* * * * *